United States Patent [19]

Gemmill et al.

[11] Patent Number: 4,584,114

[45] Date of Patent: Apr. 22, 1986

[54] MULTIFUNCTIONAL LUBRICANT ADDITIVES AND COMPOSITIONS THEREOF

[75] Inventors: Robert M. Gemmill, Pitman; Andrew G. Horodysky, Cherry Hill; Phillip S. Landis, Woodbury, all of N.J.

[73] Assignee: Mobil Oil Corporation, New York, N.Y.

[21] Appl. No.: 450,933

[22] Filed: Dec. 20, 1982

Related U.S. Application Data

[63] Continuation-in-part of Ser. No. 218,146, Dec. 19, 1980, abandoned.

[51] Int. Cl.[4] ............... C10M 133/00; C10M 135/00
[52] U.S. Cl. ............................. 252/47.5; 548/141; 548/142
[58] Field of Search ............. 252/47.5; 548/142, 141

[56] References Cited

U.S. PATENT DOCUMENTS

| | | | |
|---|---|---|---|
| 2,760,933 | 8/1956 | Fields et al. | 252/47.5 X |
| 2,836,564 | 5/1958 | Roberts et al. | 252/47.5 |
| 3,776,919 | 12/1973 | Sasse et al. | 548/141 X |
| 3,980,573 | 9/1976 | Okorodudu | 548/142 X |
| 4,136,043 | 1/1979 | Davis | 252/47.5 |
| 4,193,882 | 3/1980 | Gemmill, Jr. | 252/47.5 |

FOREIGN PATENT DOCUMENTS

28560 10/1955 Fed. Rep. of Germany ..... 252/47.5

*Primary Examiner*—William R. Dixon, Jr.
*Assistant Examiner*—Cynthia A. Prezlock
*Attorney, Agent, or Firm*—Alexander J. McKillop; Michael G. Gilman; Van D. Harrison, Jr.

[57] ABSTRACT

Mercaptothiadiazole adducts of unsaturated esters such as jojoba oil or pentaerythritol tetraoleate are highly effective multifunctional friction reducing and copper strip passivating additives for various lubricants.

8 Claims, No Drawings

MULTIFUNCTIONAL LUBRICANT ADDITIVES AND COMPOSITIONS THEREOF

CROSS REFERENCE TO RELATED APPLICATIONS

This application is a continuation-in-part of copending application Ser. No. 218,146, filed Dec. 19, 1980 now abandoned.

BACKGROUND OF THE INVENTION

1. Field of the Invention

This invention is directed to unsaturated ester-mercaptothiadiazole adducts and to lubricant compositions of improved friction reducing and corrosion-inhibiting characteristics containing same.

2. Discussion of Prior Art

In view of today's energy crisis there is a continual need for more and better means of reducing energy requirements. The use of additives to reduce or modify friction in internal combustion engines as a means of reducing such engines' fuel requirements is well known. However, the performance of prior art additives has not always lived up to their promise.

It is known from U.S. Pat. No. 2,760,933 to produce a mercaptothiadiazole ester by the reaction of the mercapto function of 2,5-dimercapto-1,3,4-thiadiazole with an acyl compound. It is also known that unsaturated organic acids, such as oleic acid, can be reacted with mercaptothiazoles [by addition of the HS function across the double bond(s)], see U.S. Pat. No. 4,193,882. Also, U.S. Pat. No. 2,836,564 teaches addition of an alpha-halogenated aliphatic monocarboxylic acid to the mercapto function. Other reactions of general interest involving mercaptothiazoles may be found in U.S. Pat. Nos. 3,776,919, 3,980,573 and 4,136,043 and German Pat. No. 28,560, dated Oct. 20, 1955. However, the adducts of this invention, to the best of applicants' knowledge, were not previously known nor were lubricant compositions containing same known.

SUMMARY OF THE INVENTION

The present invention is directed to novel adducts of unsaturated esters and mercaptothiadiazoles as novel compounds and to lubricant compositions containing a major amount of a lubricant and a friction reducing or anticorrosion amount of said adduct. The present invention is further directed to a method of reducing friction, inhibiting corrosion and reducing fuel requirements of internal combustion engines by treating the moving parts of such engines with lubricant compositions in accordance with the novel compositions of the invention embodied herein.

DESCRIPTION OF SPECIFIC EMBODIMENTS

The additives of this invention are derived for example from the reaction of 2,5-dimercapto-1,3,4-thiadiazole (DMTD) with unsaturated esters such as oleyl oleate, pentaerythritol tetraoleate and Jojoba oil. The unsaturation in the reactant ester may come from the acid or the alcohol component, or both.

The synthesis of these adducts will give reaction products which we believe will contain some of the products depicted below. As will appear below, the unsaturation can appear either in the acid or the alcohol so that the point of attachment of the mercaptothiadiazole to the ester will vary with the point of unsaturation. The products shown below, as examples, presume unsaturated acids where $R'$ is $-R^3-CH=CH-R^4$, where $R^3$ and $R^4$ may be H or an alkyl group.

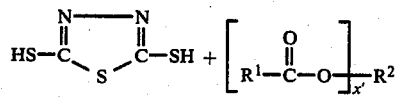

DMTD          Unsaturated Ester

Broadly, $R^1$ and $R^2$ are saturated or unsaturated groups having 1 to 44 carbon atoms and $x'$ is 1 to 4. In addition, $R^1$ can contain a $-COOH$ group. Both of $R^1$ and $R^2$ may be unsaturated, but both cannot be saturated, i.e., one of them must have at least one unsaturated bond. Each of $R^1$ and $R^2$ is selected from alkyl, cycloalkyl, aryl, aralkyl or alkaryl groups and the unsaturated members. One of the groups must have at least 10 carbon atoms and they may contain sulfur or be linked by a sulfide or polysulfide.

X is 1:

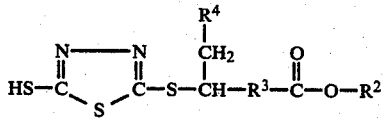

I (isomers)

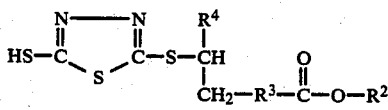

X is 2:

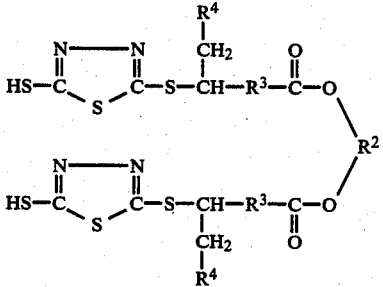

IIA
plus isomers as shown above and polymers if $R^2$ is unsaturated

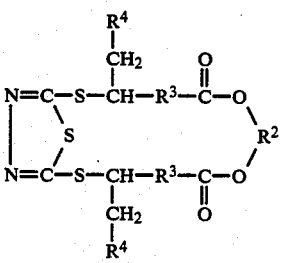

IIB
cyclic 1:1 adduct as well as polymers

It is apparent that in I the product can be fairly easily defined. However, in II the products are more complex, since the free HS-groups can further react in the same manner. It is apparent also that as the ester groups increase to 4, the molecular becomes even more complex and more difficult to define.

The alcohols used herein have the formula:

wherein y is 1 to 4 and $R^2$ is as defined hereinabove. $R^2$ will be a part of such alcohols as methyl, ethyl, propyl, hexyl, octyl, decyl, dodecyl, octadecyl alcohols, as well as such unsaturated alcohols as linoleyl and oleyl alcohols and thus $C_{21}$ to $C_{22}$ alcohol component of Jojoba oil. Similar members, to $C_{36}$ alcohols are contemplated. It is also a part of such diols as ethylene glycol and the alkanediols such as the propanediols, such triols as glycerol and such tetraols as petraerythritol.

The acids used to prepare the esters have the following formula:

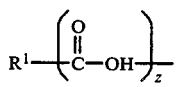

These acids include the monobasic acids where $R^1$ is defined above and z is 1 to 2. The saturated members include the ethyl, propyl, octyl, decyl and octadecyl groups or the unsaturated members such as oleyl and myristyl acid component of Jojoba oil. Some of the dibasic acids embraced are the malonic, succinic, glutaric, adipic, pimelic, suberic, azelaic and sebacic acids.

The unsaturated ester is made by choosing at least one of the acids and at least one of the alcohols, at least one of which contains at least one unsaturated bond and at least 10 carbon atoms in the hydrocarbyl chain, and reacting them at temperatures well known to the prior art. It is preferred to use stoichiometric amounts of each.

Some of the esters useful herein include those based on the monohydric alcohols such as oleyl alcohol and the polyhydric alcohols which contain at least one olefinic linkage. A non-exhaustive list of the latter includes ethylene glycol dioleate, propylene glycol dioleate, butanediol dioleate, glycerol trioleate, pentaerythritol tetraoleate, pentaerythritol trioleate monomyristate, trimethylol propane trioleate, trimethylol propane dioleate monomyristate, trimethylol propane dilinoleate monooleate and dibasic acid esters such as dioleyl adipate, dioleyl sebacate, dioleyl maleate, dioleyl succinate, dilineolyl adipate. Mixtures of the above unsaturated esters are also useful. As is noted above, at least one olefinic groups must be always present in the ester, the alkyl chain may contain two or more olefinic groups and the number of ester groups present in the unsaturated ester reactant generally should not exceed four. However, at least one of the alcohol or acid hydrocarbon chains must contain at least 10 carbon atoms.

Reaction of the ester and mercaptothiadiazole may range from a temperature of about 160° C. to about 200° C. The pressure is usually atmospheric but higher pressures may be used if desired, and usually equimolar amounts of reactants are used. However, the molar ratio of unsaturated ester to mercaptothiadiazole may vary from about 10:1 to about 1:2 and preferably 2:1 to about 1:2. The reaction normally is carried out at the above noted elevated temperatures, but suitable catalysts may be used to provide lower reaction temperatures.

The above equations depict the simplest reaction of jojoba oil and/or oleyl oleate as well as pentaerythritol tetraoleate with 2,5-dimercapto-1,3,4-thiadiazole. In the cases of oleyl oleate or jojoba oil or dibasic acid esters, it is, as is alluded to in a prior discussion, equally possible for the mercaptan group to add across the double bond of the alcohol portion of the ester, i.e.,

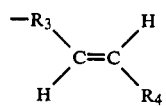

wherein $R^3$ and $R^4$ are defined hereinabove.

Statistical mixtures can provide products derived from the reaction of more than one olefin group per molecule. The reaction of both mercapto groups of 2,5-dimercapto-1,3,4-thiadiazole is dependent primarily upon the molar ratio of the reactants used and thus oligomers and mixed products thereof can be provided by this process.

Any unsaturated hydrocarbyl ester having from about 10-12 to about 75 carbon atoms may be used, depending upon oil solubility of the adduct to be synthesized. Jojoba oil is a preferred ester. Jojoba oil, a potential substitute for sperm oil, is extracted from the bean of the jojoba plant, an evergreen shrub grown in arid climates such as southwestern United States. It is essentially a mono-ester of a $C_{20}$-$C_{22}$ mono-unsaturated monocarboxylic acid and a $C_{20}$-$C_{22}$ mono-unsaturated alcohol.

DMTD (2,5-dimercapto-1,3,4-thiadiazole) is readily available from commercial sources or can be synthesized from hydrazine and carbon disulfide. Other mercaptothiadiazoles suitable for use herein include the following structures having at least one mercapto group:

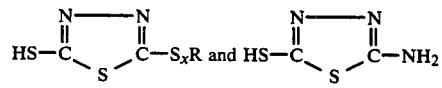

x is 1 to 3; R is H or is alkyl, alkenyl, aralkyl or alkaryl of from 1 to about 50 carbon atoms.

The amount of additive required to be effective in lubricant compositions may range from 0.1 to about 20% by weight of the total lubricant composition. Preferred is from about 0.5 to 4 wt. %. The additives of this invention reduce friction, but also may be used in combination with any conventional additives for their known purpose, e.g., dispersants, surfactants, antiwear agents, in amounts of up to about 10 wt. %.

The lubricants contemplated for use herein include both mineral and synthetic hydrocarbon oils of lubricating viscosity, mixtures of mineral and synthetic oils, or greases or other solid lubricants prepared therefrom. The synthetic hydrocarbon oils include but are not limited to long chain alkanes such as cetanes and hydrogenated olefin polymers such as trimers and tetramers of octene and decene. These synthetic oils can be mixed with other synthetic oils which include (1) ester oils such as pentaerythritol esters of monocarboxylic acids having 7 to 20 carbon atoms, (2) polyglycol ethers, (3) polyacetals and (4) siloxane fluids. Especially useful among the synthetic esters are those made from polycarboxylic acids and monohydric alcohols. More preferred are the ester fluids made from pentaerythritol and an aliphatic monocarboxylic acid containing from 7 to 20 carbon atoms, or mixtures of such acids.

Having described the invention in general terms, the following are offered as specific illustrations thereof. It is to be understood they are illustrations only and that the invention is not thereby limited except as by the appended claims.

EXAMPLE 1

Jojoba Oil Derivative of DMTD

Jojoba oil* (800.0 grams, approx. 1.3 moles) and 2,5-dimercapto-1,3-4-thiadiazole (200.0 grams, 1.3 moles) were charged to a reactor and heated to 170°–180° C. for about 7 hours under a nitrogen atmosphere. The product was cooled to room temperature and vacuum filtered through a diatomaceous clay filter aid. The finished product was a clear, dark, red-amber fluid.
*Jojoba oil is primarily a mixture of esters of $C_{20}$–$C_{22}$ mono-unsaturated acids and alcohols.

|  | Found | Calc. |
|---|---|---|
| Wt. % Oxygen | 4.4 | 4.3 |
| Wt. % Nitrogen | 3.4 | 3.7 |
| Wt. % Sulfur | 11.0 | 12.8 |

EXAMPLE 2

Oleyl Oleate Derivative of DMTD

Oleyl oleate (100.0 grams, 0.19 mole) and 2,5-dimercapto-1,3,4-thiadiazole (28.1 grams, 0.19 mole) were charged to a reactor and heated to 170°–180° C. for 4 hours under a nitrogen atmosphere. The product was cooled to room temperature and vacuum filtered through a diatomaceous clay filter aid. The finished product was a clear, dark red-amber fluid.

EXAMPLE 3

Pentaerythritol tetraoleate - DMTD Adduct

Approximately 355 grams pentaerythritol tetraoleate (made by reaction of pentaerythritol with 4 moles of oleic acid) and 25 grams 2,5-dimercapto-1,3,4-thiadiazole were charged to a reactor and heated to 170°–180° C. for 2½ hours with agitation under a nitrogen atmosphere. The product was cooled to approximately 80°–90° C. and filtered over diatomaceous earth yielding a clear brown fluid with a viscosity of 36.5 cSt @ 100° C. The product contained:
Sulfur, Wt. %—4.1
Nitrogen, Wt. %—1.3
Carbon, Wt. %—71.9
Hydrogen, Wt. %—11.0

EXAMPLE 4

Pentaerythritol tetraoleate - DMTD Adduct

Approximately 320 grams pentaerythritol tetraoleate and 35 grams 2,5-dimercapto-1,3,4-thiadiazole were reacted for 3 hours @ 180°–185° C. under nitrogen atmosphere as described generally in Example 3. The product was cooled to approximately 80°–90° C. and filtered over diatomaceous earth yielding a clear brown fluid with a viscosity of 57.5 cSt @ 100° C. The product contained:

Sulfur, Wt. %—5.8
Nitrogen, Wt. %—1.9
Carbon. Wt. %—69.8
Hydrogen, Wt. %—10.6

EXAMPLE 5

Pentaerythritol tetraoleate - DMTD Adduct

Approximately 240 grams pentaerythritol tetraoleate and 45 grams 2,5-dimercapto-1,3,4-thiadiazole were reacted for 4 hours @ 180°–190° C. with a nitrogen purge as generally described in Example 3. The product was cooled to approximately 80° C. and filtered over diatomaceous earth yielding a clear brown viscous product. The product contained:
Sulfur, Wt. %—9.6
Nitrogen, Wt. %—2.8
Carbon, Wt. %—69.1
Hydrogen, Wt. %—9.9

The products of the above examples were evaluated using Low Velocity Friction Apparatus (LVFA) at 4 wt. % concentration in a fully formulated 5W-20 synthetic automotive engine oil containing dispersant, detergent and inhibitor package. The oil had the following general characteristics: KV @ 100° C. - 6.8 cs, KV @ 40° C. - 36.9 cs, Viscosity Index - 143. Results reported in Table 1 refer to percent reduction in coefficient of friction as compared to the unmodified oil using the LVFA.

Low Velocity Friction Apparatus (LVFA)

The Low Velocity Friction Apparatus is used to measure the coefficient of friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ⅓ HP electric motor. To vary the sliding speed, the output speed of the transmission is regulated by a lever-cam-motor arrangement.

Procedure

The rubbing surfaces and 12–13 ml. of test lubricant are placed on the LVFA. A 500 psi load is applied, and the sliding speed is maintained at 40 fpm at ambient temperature for a few minutes. A plot of coefficients of friction ($U_k$) over a range of sliding speeds, 5 to 40 fpm (25–195 rpm), is obtained. A minimum of three measurements is obtained for each test lubricant. Then, the test lubricant and specimens are heated to 250° F., another set of measurement is obtained, and the system is run for 50 minutes at 250° F., 500 psi, and 30 fpm sliding speed. Freshly polished steel specimens are used for each run. The surface of the steel is parallel ground to 6 to 8 microinches. The percentages by weight are percentages by weight of the total lubricating oil composition, including the usual additive package. The data are percent decrease in friction according to:

$$\frac{(U_k \text{ of oil alone} - U_k \text{ of Additive plus oil})}{(U_k \text{ of oil alone})} \times 100$$

Thus, the value for the oil alone would be zero for the form of data used in the Table below.

TABLE 1

| | Friction Reduction Tests | |
|---|---|---|
| | Additive Conc. | % Red. in Coeff. of Friction at indicated sliding speed |
| | Wt. % | 5 Ft./Min. | 30 Ft./Min. |
| Test Oil | 0 | 0 | 0 |
| Example 1 | 4 | 22 | 38 |
| Example 2 | 4 | 10 | 10 |
| Example 4 | 4 | 15 | 9 |
| Example 5 | 4 | 12 | 8 |

The products of the examples were also tested for copper corrosivity using ASTM No. D-130-6 at 250° F. for 3 hours and D-130-9 at 210° F. for 6 hours.

Copper Corrosion Test

The test employed for this purpose was a standard ASTM Test D-130 which, in general, comprises immersion of a polished copper strip in the material to be tested for a period of 3 hrs. at a temperature of 250° F. At the end of this period the copper strip is removed, washed, and rated for degree of corrosion by comparison with the ASTM standard strips. Test data is reported in Table 2. The concentration of the respective examples is in Wt. % in 200" SPN, i.e., 200 second solvent paraffinic neutral.

TABLE 2

| | Copper Strip Corrosion Tests | | |
|---|---|---|---|
| | Conc. Wt. % in 200" SPN | D-130-6 250° F., 3 Hrs. | D-130-9 210° F., 6 Hrs. |
| Example 1 | 1 | 1A | 1A |
| | 3 | 1A | 1A |
| Example 2 | 1 | 2A | 2A |
| | 3 | 1B | 1B |
| Example 3 | 1 | 1A | 1A |
| | 3 | 1A | 1A |
| Example 4 | 1 | 1A | 1A |
| | 3 | 1A | 1A |

Fuel efficient lubricating oils are of great importance due to the current world petroleum situation. Ashless friction reducing additives not containing phosphorus or heavy metals are desirable from an environmental standpoint as well as a fuel conservation standpoint. Control of copper corrosion is an added dimension to friction modifiers. Also, since jojoba plants, the preferred embodiment, can be grown in desert areas with little rainfall, it is likely that availability and economy will improve with time. The union of two such diverse moieties as DMTD and an unsaturated ester results in an adduct possessing an unexpected combination of properties not attainable by any known combination or admixture of reactants. The effectiveness of this combination is fully supported by the data in the Tables.

It is apparent to those of ordinary skill in the art that variations and departures from the exemplary matter described herein can be readily made within the scope of the specification and the appended claims.

We claim:

1. A lubricant composition comprising a major proportion of an oil of lubricating viscosity or grease prepared therefrom and a minor proportion sufficient to impart friction reducing and anti-corrosion properties to said composition of an adduct of an unsaturated ester selected from the group consisting of jojoba oil, oleyl oleate, and pentaerythritol tetraoleate and a mercaptothiadiazole, in a molar ratio of ester to mercaptothiadiazole of from about 10:1 to about 1:2 and at a temperature of from about 160° C. to about 200° C. wherein said mercaptothiadiazole has the general formulas:

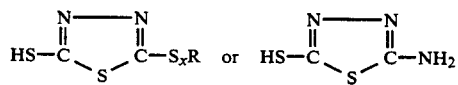

where x is 1 to 3, R is H or is alkyl, alkenyl, aralkyl or alkaryl of from 1 to about 50 carbon atoms.

2. The lubricant composition of claim 1 where said unsaturated ester is jojoba oil.

3. The lubricant composition of claim 1 where said unsaturated ester is oleyl oleate.

4. The lubricant composition of claim 1 where said unsaturated ester is pentaerythritol tetraoleate.

5. An adduct prepared by reacting an unsaturated ester selected from the group consisting of jojoba oil, oleyl oleate and pentaerythritol tetraoleate and a mercaptothiadiazole, in a molar ratio of ester to mercaptothiadiazole of from about 10:1 to about 1:2 and at a temperature of from about 160° C. to about 200° C. wherein said mercaptothiadiazole has the general formulas:

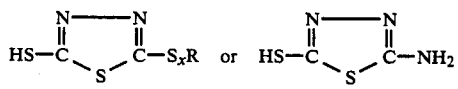

where x is 1 to 3; R is H or is alkyl, alkenyl, aralkyl or alkaryl of from 1 to about 50 atoms.

6. The adduct of claim 5 wherein said ester is jojoba oil and said mercaptothiadiazole is 2,5-dimercapto-1,3-4-thiadiazole.

7. The adduct of claim 5 wherein said ester is oleyl oleate and said mercaptothiadiazole is 2,5-dimercapto-1,3-4-thiadiazole.

8. The adduct of claim 5 wherein said ester is pentaerythritol tetraoleate and said mercaptothiadiazole is 2,5-dimercapto-1,3-4-thiadiazole.

* * * * *